United States Patent [19]

Elinkmann et al.

[11] 4,377,703

[45] Mar. 22, 1983

[54] PROCESS FOR PREPARING BENZOXANTHENE AND BENZOTHIOXANTHENE DYESTUFFS

[75] Inventors: Hans-Gerd Elinkmann, Frankfurt am Main; Emmerich Paszthory, Hofheim am Taunus, both of Fed. Rep. of Germany

[73] Assignee: Hoechst Aktiengesellschaft, Frankfurt am Main, Fed. Rep. of Germany

[21] Appl. No.: 319,047

[22] Filed: Nov. 6, 1981

Related U.S. Application Data

[63] Continuation of Ser. No. 154,320, May 29, 1980, abandoned.

[30] Foreign Application Priority Data

Jun. 1, 1979 [DE] Fed. Rep. of Germany ....... 2922374

[51] Int. Cl.$^3$ ................. C07D 335/04; C07D 311/78
[52] U.S. Cl. ...................................... 549/24; 549/382
[58] Field of Search ........................... 549/25, 24, 382; 260/345.3

[56] References Cited

U.S. PATENT DOCUMENTS 3,781,302 12/1973 Fuchs et al. ......................... 549/25

FOREIGN PATENT DOCUMENTS 2025291 12/1971 Fed. Rep. of Germany ........ 549/24
19872 5/1980 European Pat. Off. .............. 549/24

Primary Examiner—Joseph Paul Brust
Attorney, Agent, or Firm—Curtis, Morris & Safford

[57] ABSTRACT

Mixtures of isomers of benzoxanthene and benzothioxanthene dyestuffs of the formulae

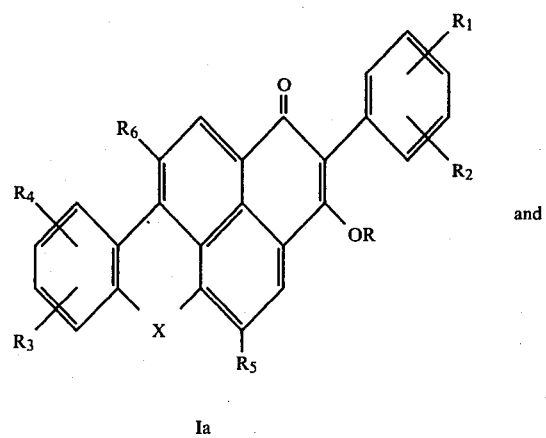

and

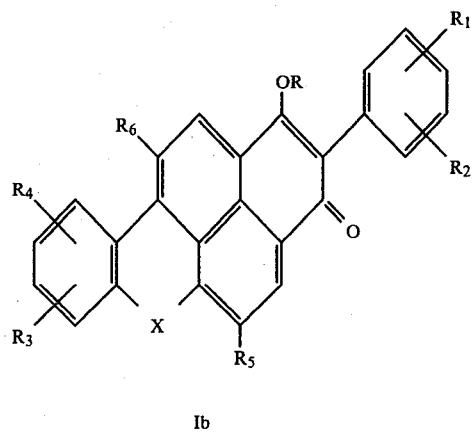

wherein X is oxygen or sulfur, R optionally substituted alkyl, acyl or arylsulfonyl, $R_1$ and $R_2$ are hydrogen or halogen, alkyl, aryl, acyl, acyloxy, carbalkoxy, alkoxy, nitro, alkylthio or alkylsulfonyl or they form together a condensed benzene ring, $R_3$ and $R_4$ are hydrogen or halogen, alkyl, alkoxy, aryl, carbalkoxy or nitrile, $R_5$ and $R_6$ are hydrogen or optionally substituted alkoxy, are obtained by condensing the corresponding benzoxanthene or benzothioxanthene-3,4-carboxylic acid anhydrides or esters with phenyl acetic acid anhydrides or esters in the presence of alkali at a temperature of about 150° to 260° C. and alkylating or acylating the so-obtained hydroxy intermediates without previous isolation thereof when condensation and alkylation or acylation are performed in a polar organic solvent.

7 Claims, No Drawings

PROCESS FOR PREPARING BENZOXANTHENE AND BENZOTHIOXANTHENE DYESTUFFS

This is a continuation of application Ser. No. 154,320 filed May 29, 1980, now abandoned.

It is known from U.S. Pat. No. 3.781.302—which is hereby incorporated by reference—to prepare mixtures of isomers of benzoxanthene or benzothioxanthene dyestuffs of the general formulae

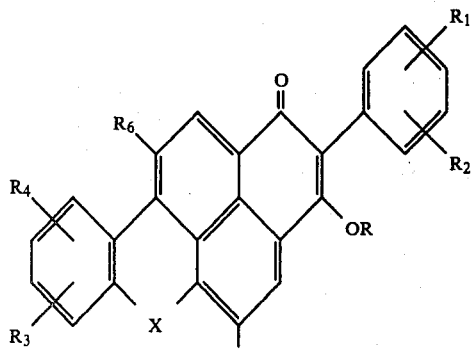

Ia

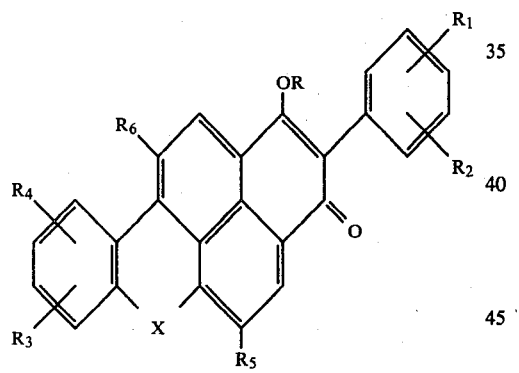

Ib wherein X is oxygen or sulfur, R is an optionally substituted alkyl group, an acyl or arylsulfonyl group, $R_1$ and $R_2$ are hydrogen or halogen atoms, alkyl, aryl, acyl, acyloxy, carbalkoxy, alkoxy, nitro, alkylthio or alkylsulfonyl groups or they form together a condensed benzene ring, $R_3$ and $R_4$ are hydrogen or halogen atoms, alkyl, alkoxy, aryl, carbalkoxy or nitrile groups, $R_5$ and $R_6$ represent hydrogen or optionally substituted alkoxy groups, by heating to a temperature from about 150° to 260° C., in the present of alkaline agents, benzoxanthene or benzothioxanthene-3,4-dicarboxylic acid anhydrides of the general formula II or the derivatives thereof of the general formula III

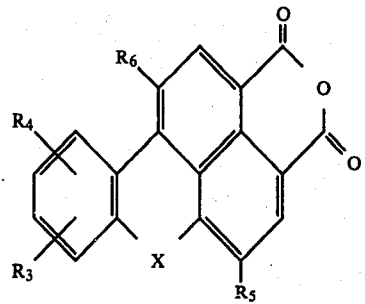

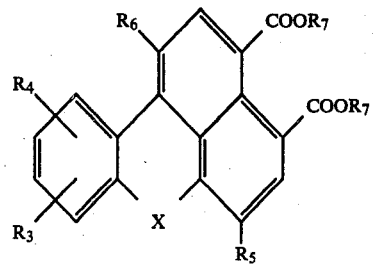

wherein X, $R_3$, $R_4$, $R_5$ and $R_6$ have the above meanings and $R_7$ is hydrogen or alkyl, such as methyl, with a compound of the formulae IV and/or V

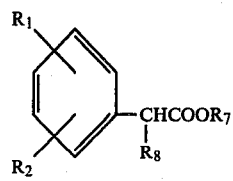

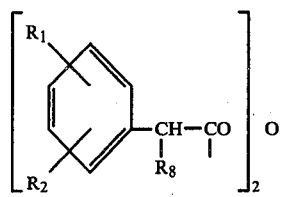

wherein $R_1$, $R_2$ and $R_7$ have the meanings given above, and $R_8$ is hydrogen or hydroxy, and by alkylating or acylating the so-obtained compounds consisting of the mixture of isomers of the general formulae VIa and VIb.

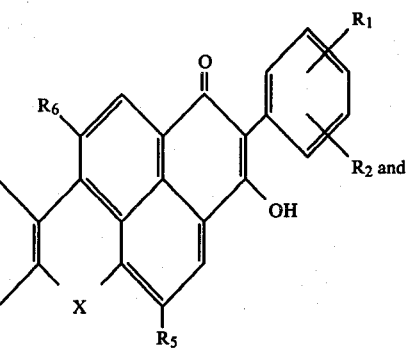

VIa

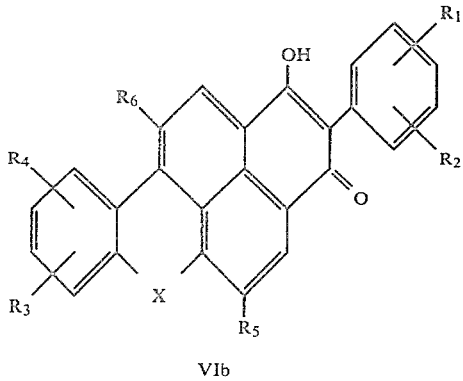

VIb wherein X, $R_1$, $R_2$, $R_3$, $R_4$, $R_5$ and $R_6$ have the above meanings.

The condensation of the compounds II or III with the compounds of the formulae IV or V in most of the examples is carried out in the melt, but can also take place in a polar solvent, such as N-methylpyrrolidone. The resulting intermediate, that is the isomer mixture of the formulae VIa and VIb, is isolated in any case, prior to being alkylated or acylated. These intermediates, however, have extremely bad filtration properties, so that this isolation process requires a considerable expenditure on time and apparatus.

It has now been found that the compounds of the formulae Ia and Ib can be obtained especially advantageously by carrying out the condensation and alkylation or acylation without isolating the intermediates. It is surprising that this significant simplification of the process hoes not result in a deterioration of the yield or the purity of the final product.

Subject of the present invention is, therefore, a process for preparing the above characterized mixtures of isomers consisting of compounds of the formulae Ia and Ib by heating compounds of the formulae II or III with compounds of the formulae IV and/or V in the presence of an alkali at temperatures between about 150° and about 260° C. and by subsequently alkylating or acylating the mixture of isomers of the formulae VIa and VIb, which comprises carrying out these reactions in a polar organic solvent without isolation of the mixture of isomers of the formulae VIa and VIb. Examples of suitable polar solvents are those mentioned in U.S. Pat. No. 3,781,302, preferably N-methylpyrrolidone. Apparently the solvent must be stable at the reaction temperature, even to the alkali present, and be inert towards the reaction partners, that means, it must not have an alkylating or acylating action and it must not be capable of being alkylated or acylated. The boiling point of the solvent preferably lies above the reaction temperature, because this facilitates the separation of volatile byproducts.

The alkali necessary for condensation can be an alkalimetal hydroxide, carbonate or acetate. Potassium acetate and potassium carbonate are preferred.

Condensation is carried out preferably in the presence of potassium acetate or potassium carbonate in N-methylpyrrolidone at a temperature from 200° to 210° C. The reaction solution obtained can directly be reacted ewith the alkylating or acylating agent.

If the condensation is carried out in the presence of an alkalimetal acetate, it is recommended to separate the released acetic acid, if an alkylation reaction is intended with alkylating agents which can react with this acetic acid, for example dialkylsulfates. Otherwise, it would not only be necessary to use greater quantity of alkylating agents, but the resulting acetic ester would also act as precipitant for the intermediate of the formulae VIa and VIb.

The alkylation and acylation is performed in the manner usual for phenolic compounds. Appropriate alkylating agents are especially the dialkylsulfates, above all lower dialkylsulfates as dimethylsulfate or diethylsulfate, alkylhalides such as methyl chloride or benzyl chloride, alkylene oxides such as ethylene oxide or propylene oxide and arylsulfonic acid esters such as p-toluene sulfonic acid methyl ester. Examples of suitable acylating agents are aliphatic or aromatic carboxylic or sulfonic acid chlorides or carboxylic acid anhydrides such as acetyl chloride, propionyl chloride, benzoyl chloride, benzene sulfonic acid chloride or acetic anhydride.

For isolating the final product from the reaction solution this solution is suitably cooled and a precipitant is added. Suitable precipitants are organic liquids miscible with the reaction medium in which the dyestuff is difficultly soluble and which can easily be separated from the reaction medium. Lower alkanols, especially methanol, are suitable.

The dyestuffs are obtained in a high yield and in the high purity necessary for fluoroescent dyestuffs.

The invention will be explained in detail by the following examples. Percentages are by weight, unless otherwise stated.

EXAMPLE 1

In a vessel provided with a stirrer a mixture of 400 kg N-methylpyrrolidone, 104.6 kg phenyl acetic acid and 62.8 kg potassium acetate is heated to 80° C. while stirring. Subsequently there are added 196 kg benzothioxanthene-3,4-dicarboxylic acid anhydride and the mixture is heated for 2 hours to 180° C. After continuous stirring for 1 hour at 180° C., the temperature is increased to 200°-210° C. and stirring is continued at this temperature for another 8-10 hours.

After completing this reaction, 63 kg of 50% sulfuric acid are added within 30 minutes at 200° C. The mixture is cooled to 120° C. and acetic acid and water are distilled off at about 120°-130° C. and under about 65 to 95 mbar (50-70 torr) up to a head temperature of 130° C. at 80 mbar (60 torr).

When the distillation is finished, 300 kg N-methylpyrrolidone and 68.2 kg potassium carbonate are added. Stirring of the mixture is continued for 30 minutes at 120° C. and then the mixture is cooled to 80° to 85° C. A further 14 kg of potassium carbonate are added and the mixture is methylated with 160 kg dimethyl sulfate within 1 to 2 hours at 80° to 85° C. After having finished this reaction, stirring is continued for 2 hours at 80°-85° C., the product is subsequently precipitated with 400 kg methanol at 30°-40° C. and isolated in a pressure filter at 150° C. A blueish red, highly fluorescent dyestuff, consisting of an isomer mixture of the formulae

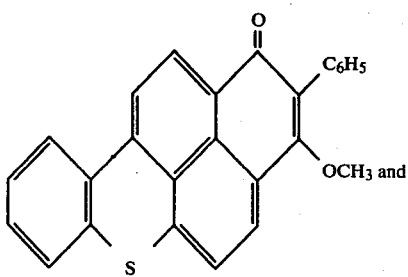

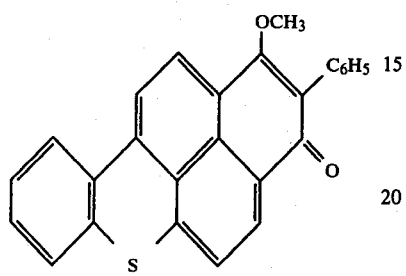

is obtained in a good yield.

EXAMPLE 2

In a vessel provided with a stirrer 76 kg benzothioxanthene-3,4-dicarboxylic acid anhydride, 37.5 kg phenyl acetic acid, 25 kg potassium acetate and 200 kg N-methylpyrrolidone are heated to 180° C. After 1 hour of stirring at 180° C. the temperature is increased to 200° C. and stirring is continued for 6 hours at this temperature.

When this reaction is terminated, the reaction mixture is cooled to 110° C., 75 kg acetic anhydride are added dropwise within 20 minutes and stirring is continued for 2 hours at 110° C. Subsequently the mixture is cooled to 20° C., 200 liters of methanol are added, stirring is continued for 1 hour and the product is isolated on a pressure filter. A pure, blueish red fluorescent dyestuff is obtained in a good yield, consisting of an isomer mixture of the formulae

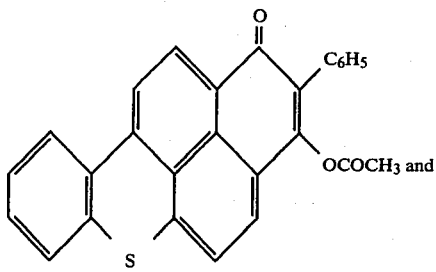

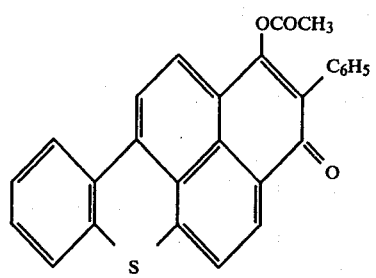

EXAMPLE 3

79.5 kg of 10-methoxy-benzoxanthene-3,4-dicarboxylic acid anhydride, 37.5 kg phenyl acetic acid, 25 kg potassium acetate and 200 kg N-methylpyrrolidone are introduced into a vessel provided with a stirrer. The mixture is heated with stirring to 180° C. within 2 hours, stirring is continued for 1 hour, then the mixture is rapidly heated to 200° C. and stirring is continued for another 6 hours at this temperature. When the reaction is complete, the mixture is cooled to 110° C., 75 kg acetic anhydride are added dropwise within 20 minutes and stirring is continued for 2 hours at 110° C. Subsequently, the mixture is cooled to 20° C., 200 liters of methanol are added, stirring is continued for 1 hour and the product is isolated on a pressure filter. A pure orange yellow highly fluorescent dyestuff is obtained in good yield, consisting of an isomer mixture of the formulae

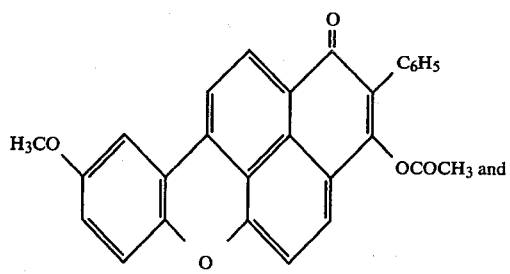

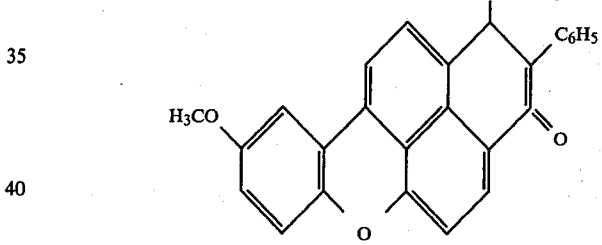

EXAMPLE 4

In a vessel provided with stirrer a mixture of 79.5 kg 10-methoxybenzoxanthene-3,4-dicarboxylic acid anhydride, 37.5 kg phenyl acetic acid, 25 kg potassium acetate and 200 kg N-methylpyrrolidone is heated to 180° C. while stirring. After continuing stirring for 1 hour at 180° C., the temperature is increased to 200° C. and at this temperature stirring is maintained for 8 hours.

When the reaction is complete 25.4 kg 50% sulfuric acid are added at 190°–200° C. within 25 minutes. The mixture is cooled to 120° C., and acetic acid and water are distilled off at 120°–160° C. and under about 65 to 95 mbar (50–70 torr) up to a head temperature of 160° C. at 80 mbar (60 torr).

When the distillation is finished, 12 kg N-methylpyrrolidone are added and 27.5 kg potassium carbonate are introduced within 25 minutes at 120° to 123° C. Stirring of the mixture is continued for 30 minutes at 120° C. and then the mixture is cooled to 80°–85° C. A further 5.6 kg potassium carbonate are added and the product is methylated at 80° C. with 60.5 kg dimethyl sulfate for 1–2 hours. After finishing this reaction, stirring is continued for 2 hours at 80°–85° C., subsequently the product is precipitated at 65° C. with 161 kg methanol, the mixture is cooled to 5°–10° C., stirring is continued for 1 hour and the dyestuff is isolated on a pressure filter. An orange yellow, fluorescent dyestuff, consisting of an isomer mixture of the formulae

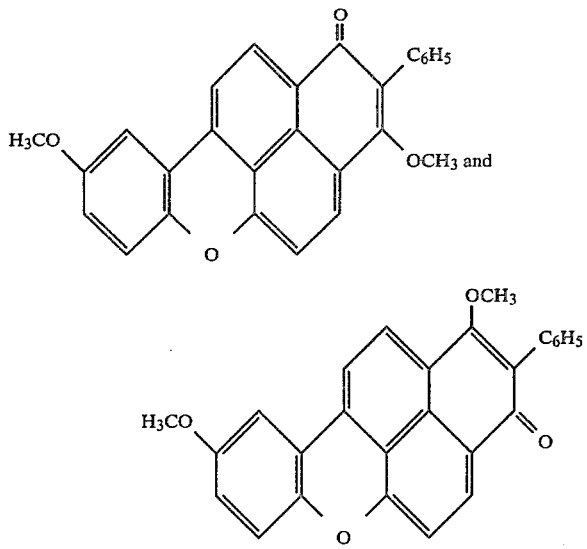

is obtained in a good yield.

EXAMPLE 5

A mixture of 400 kg α-chloronaphthalene, 104.6 kg phenyl acetic acid and 62.8 kg potassium acetate is heated while stirring to 80° C. in a vessel provided with a stirrer. Subsequently there are added 196 kg benzothioxanthene-3,4-dicarboxylic acid anhydride and the mixture is heated to 180° C. for 2 hours. After a continued stirring of 1 hour at 180° C. the mixture is heated to 200°–210° C. and stirring continued for 8–10 hours at this temperature.

After finishing the reaction according to Example 1, 63 kg of 50% sulfuric acid are added within 30 minutes at 190°–200° C. The mixture is cooled to 120° C. and acetic acid and water are distilled off at 120°–130° C. and under about 65 to 95 mbar (50–70 torr) up to a head temperature of 130° C. at 80 mbar (60 torr).

Upon complete distillation, 300 kg α-chloro-naphthalene are added and the product is methylated within 1–2 hours with 160 kg dimethyl sulfate at 80°–85° C. When this reaction is finished, stirring is continued for 2 hours at 80°–85° C. and subsequently the product is precipitated with 400 kg methanol at 30° C.–40° C. and isolated on a pressure filter at 15° C. The blueish red pure intensively fluorescent dyestuff of Example 1 is obtained in good yield.

EXAMPLE 6

In a vessel provided with a stirrer there are heated while stirring 76 kg benzothioxanthene-3,4-dicarboxylic acid anhydride, 37.5 kg phenyl acetic acid anhydride, 25 kg potassium acetate and 200 kg hexamethyl phosphoric acid trisamide to 180° C. After continuing stirring for 1 hour at 180° C., the temperature is increased to 200° C. and stirring is continued at this temperature for 6 hours.

After finishing this reaction, the product is cooled to 110° C. 75 kg Acetic anhydride are added within 20 minutes and stirring is continued for 2 hours at 110° C. Subsequently the mixture is cooled to 20° C., 200 liters of methanol are added, stirring is continued for 1 hour and the product is isolated on a pressure filter. The pure, blueish red fluorescent dyestuff according to Example 2 is obtained in a good yield.

What is claimed is:

1. In an industrial process for the manufacture of a mixture of a benzoxanthene or benzothioxanthene dyestuff of the formula

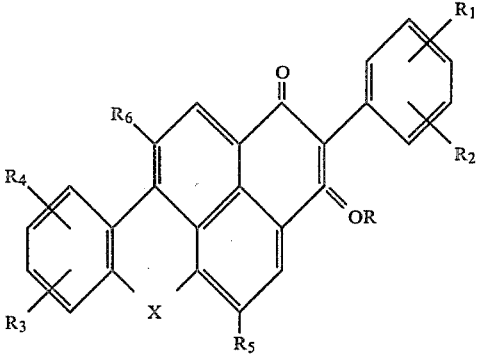

with its isomer of the formula

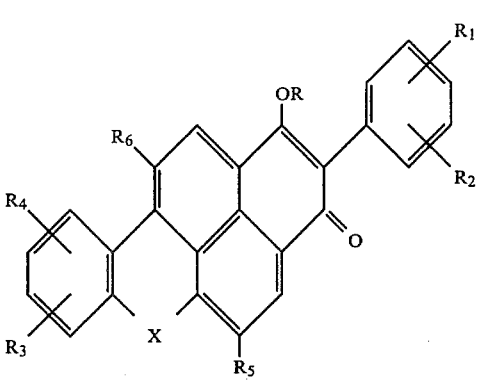

wherein X is oxygen or sulfur, R is alkyl of 1 to 20 carbon atoms, alkyl of 1 to 20 carbom atoms which may be substituted by chlorine, bromine, alkoxy of 1 to 4 carbon atoms, hydroxy, cyano or phenyl, benzoyl, alkanoyl of 1 to 20 carbon atoms, benzene sulfonyl or p-toluene sulfonyl, $R_1$ and $R_2$ are hydrogen, chlorine, bromine, phenyl, alkyl of 1 to 20 carbon atoms, alkanoyloxy of 1 to 4 carbon atoms, alkoxy of 1 to 4 carbon atoms, alkoxycarbonyl of 2 to 5 carbon atoms, nitro, alkylthio of 1 to 4 carbon atoms or alkylsulfonyl of 1 to 4 carbon atoms or, when together and adjacent, are —CH=CH—CH=CH— to form a fused benzene ring, $R_3$ and $R_4$ are hydrogen, chlorine, bromine, cyano, carbalkoxy of 1 to 4 carbon atoms, phenyl, alkyl of 1 to 4 carbon atoms of alkoxy of 1 to 4 carbon atoms and $R_5$ and $R_6$ are hydrogen, alkoxy of 1 to 4 carbon atoms, alkoxy of 1 to 4 carbon atoms which may be substituted by chloro, bromo, hydroxy, alkanoyloxy of 1 to 4 carbon atoms or phenyl by heating to a temperature in the range of 150° C. to 260° C., in the presence of an alkaline agent selected from the group consisting of alkali metal hydroxide, carbonate or acetate a benzoxanthene or benzothioxanthene-3,4-dicarboxylic acid anhydride of the formula

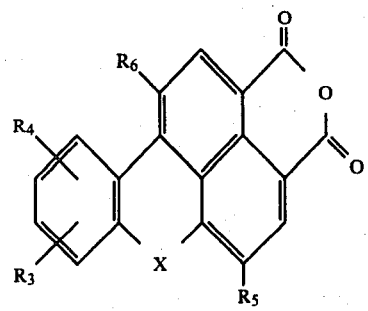

or the derivatives thereof of the formula

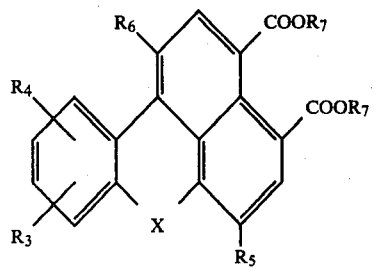

wherein X, $R_3$, $R_4$, $R_5$ and $R_6$ are as defined above and $R_7$ is hydrogen or alkyl, with a compound of the formula

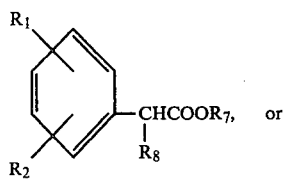

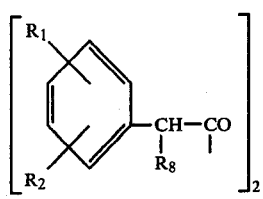

wherein $R_1$, $R_2$ and $R_7$ are as defined above and $R_8$ is hydrogen or hydroxy, and by alkylating or acylating the compounds formed consisting of an isomer mixture of a compound of the formula

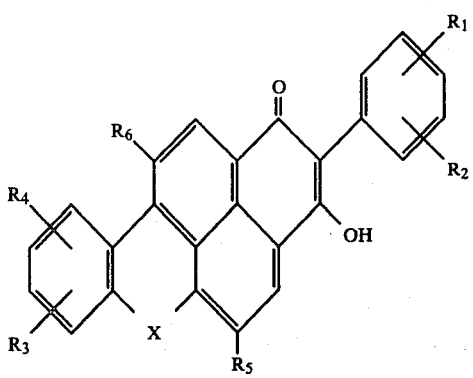

and of the formula

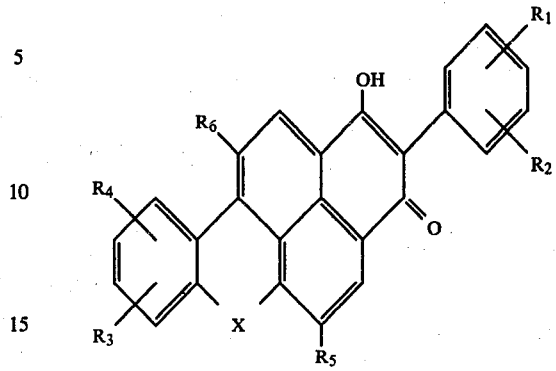

wherein X, $R_1$, $R_2$, $R_3$, $R_4$, $R_5$ and $R_6$ and are as defined above, the improvement which comprises conducting the process in a polar organic solvent selected from the group consisting of dimethyl formamide, dimethyl acetamide, N-methylpyrrolidone, hexamethyl phosphoric acid trisamide, dimethyl sulfoxide, o-dichlorobenzene, nitrobenzene and α-chloronaphthalene without isolating the isomer mixture of the intermediates containing hydroxy groups.

2. The process of claim 1, wherein said benzoxanthene or benzothioxanthene-3,4-dicarboxylic acid anhydride of the formula

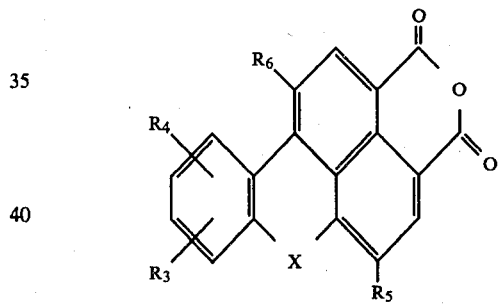

or the derivatives thereof of the formula

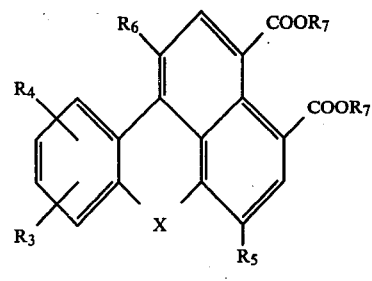

is heated with one or both compounds of the formula

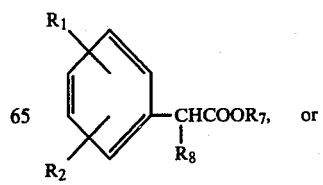

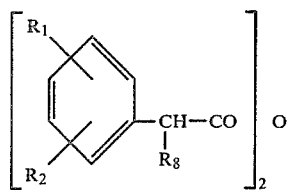

to a temperature in the range of 200° C. to 210° C.

3. The process as claimed in claim 1, wherein the polar solvent is N-methylpyrrolidone.

4. The process as claimed in claim 1, wherein the alkaline agent is potassium carbonate or acetate.

5. The process as claimed in claim 1, wherein alkylating is performed by means of a lower dialkylsulfate, a lower alkyl chloride, benzyl chloride, a lower alkylene oxide or a lower alkyl ester of benzene or p-toluene sulfonic acid.

6. The process as claimed in claim 1, wherein acylating is performed by means of a lower alkanoyl chloride, a lower alkanoic acid anhydride, benzoyl chloride or benzene sulfonyl chloride.

7. The process as claimed in claim 1, wherein the product is precipitated from the reaction solution with a lower alkanol.

* * * * *